United States Patent [19]

Nielsen

[11] 4,167,527

[45] Sep. 11, 1979

[54] METHANOL OXIDATION/DEHYDROGENATION OVER SILVER-GOLD ALLOY

[75] Inventor: Norman A. Nielsen, Wilmington, Del.

[73] Assignee: E. I. Du Pont de Nemours and Company, Wilmington, Del.

[21] Appl. No.: 871,594

[22] Filed: Jan. 23, 1978

[51] Int. Cl.² ............................................. C07C 45/16
[52] U.S. Cl. ................................. 260/603 C; 260/606
[58] Field of Search ................... 260/603, 603 R, 606, 260/603 C

[56] References Cited

U.S. PATENT DOCUMENTS

| 3,086,852 | 4/1963 | Fenske | 260/603 R |
| 3,956,191 | 5/1976 | Cusumano | 252/474 |

FOREIGN PATENT DOCUMENTS 610699 12/1960 Canada .................................... 260/603

OTHER PUBLICATIONS

Thomas, J.A.C.S., vol. 42, No. 5, pp. 867–882.

Primary Examiner—Werren B. Lone

[57] ABSTRACT

This invention relates to a process for the catalytic conversion of methanol to formaldehyde by oxidation/dehydrogenation over a silver-gold alloy catalyst.

12 Claims, 1 Drawing Figure

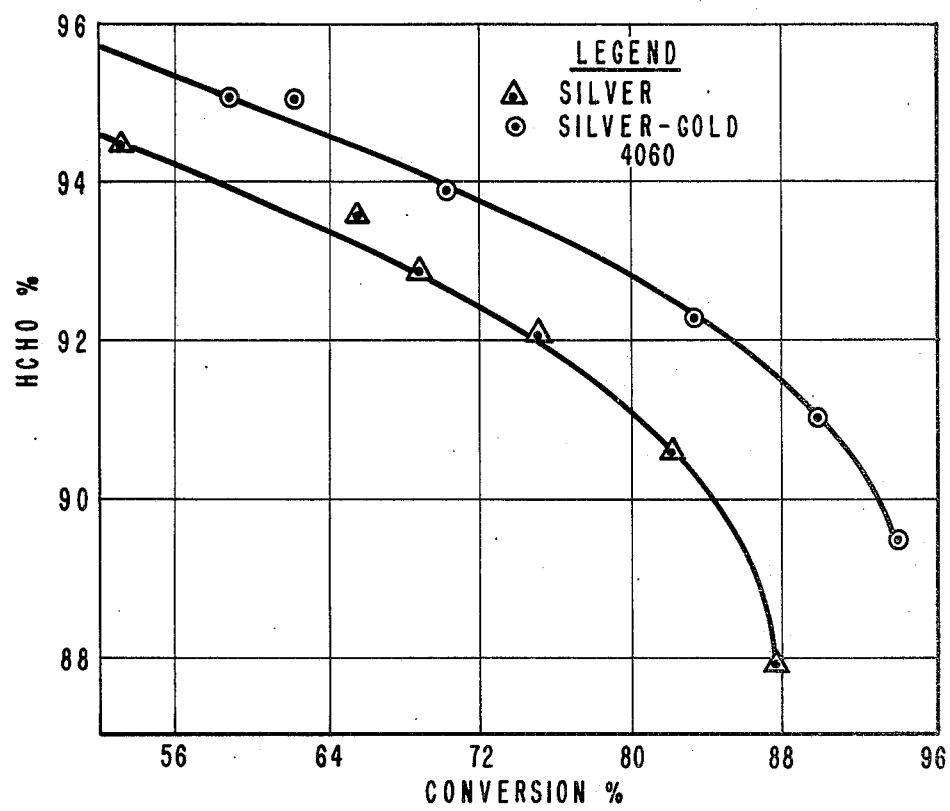

METHANOL OXIDATION/DEHYDROGENATION OVER SILVER-GOLD ALLOY

FIELD OF THE INVENTION

This invention relates to a process for the catalytic conversion of methanol to formaldehyde. In particular, the invention relates to such a process in which the catalyst is a silver-gold alloy.

BACKGROUND OF THE INVENTION

The reaction by which formaldehyde is obtained from methanol by catalytic oxidation has been known since 1878 and the use of silver catalysts for this purpose has been known at least since 1908 as is disclosed in German Pat. No. 228,687. Though other catalytic metals and metal oxides have been proposed and used, the use of silver for this process is quite widespread.

There are two commercially accepted processes. The first utilizes a silver catalyst and operates in an oxygen deficient atmosphere. The second utilizes a metal oxide catalyst and operates in a methanol deficient atmosphere. The first method for carrying out the process involves passing a mixture of methanol vapor and air over a stationary catalyst at approximately atmospheric pressure and absorbing the product gases in water. The mechanism is believed to be a combination of two reactions involving the dehydrogenation and oxidation of methanol:

$$CH_3OH \rightarrow HCHO + H_2$$

$$CH_3OH + \tfrac{1}{2}O_2 \rightarrow HCHO + H_2O.$$

It is desirable to provide a catalyst which is very selective in promoting the formation of formaldehyde while at the same time minimizing side reactions which result in the formation of CO and $CO_2$.

Silver-catalyzed processes for making formaldehyde from methanol can be characterized according to the number of catalytic stages used to effect the conversion. Single stage operation is quite widely used but suffers from the disadvantage that rather high amounts of unconverted methanol are contained in the product emerging from the catalyst bed. This phenomenon is customarily referred to as "methanol leakage". Since for many applications methanol is an undesirable contaminant, it must be separated from the formaldehyde solution. This entails a substantial investment in distillation facilities and energy to carry out such separations. It is usually necessary that the methanol content of the product be no greater than 2% by weight.

One way of eliminating the need for facilities to distill off methanol is to use two catalytic stages with interstage cooling. A basic two-stage process of this type was disclosed in U.S. Pat. No. 2,462,413 to Meath. In Northeimer's U.S. Pat. No. 3,959,383, an improvement on the Meath process is disclosed by which even lower amounts of methanol in the product can be obtained.

SUMMARY OF THE INVENTION

It has now been discovered that the yield of formaldehyde is increased in either the single or dual silver catalyzed reactor system by using a silver-gold alloy catalyst. In addition, the silver-gold alloy catalyst has a longer operating life than silver because the selectivity towards formaldehyde production decreases more slowly and the rate of carbon deposition on the catalyst is reduced. Furthermore, less sintering of the catalyst occurs which lowers the rate of pressure drop build-up and allows longer operating life and makes spent catalyst removal easier. The aforementioned comparative improvements are with respect to the standard silver catalyst presently common in commercial plants that operate in an oxygen deficient atmosphere.

DISCUSSION OF THE PRIOR ART

Although silver is usually used in commercial oxygen deficient formaldehyde processes, patents have also disclosed the use of some alloy catalysts, such as silver-copper (U.S. Pat. No. 2,939,883), silver-cadmium (U.S. Pat. No. 3,334,143) and silver-thallium (Can. Pat. No. 661,089). It is also known that gold is a catalyst for converting methanol to formaldehyde but it is not commercially practical because it is very active in decomposing formaldehyde (Thomas, Moyer D., Preparation of Formaldehyde, Journal of the American Chemical Society, Vol. 42, pp. 867-882, 1920).

DESCRIPTION OF THE DRAWING

FIG. 1 displays the % conversion of methanol versus the yield of formaldehyde for a standard silver catalyst and for a silver-gold alloy catalyst (60 atomic % gold) in a single stage reactor. The data used in drawing this figure are contained in Examples 3 and 9-19.

DETAILED DESCRIPTION OF THE INVENTION

Catalysts of the invention can be made in any convenient manner and ordinarily an alloy with silver and gold will be prepared simply by melting the two components together in the desired proportions. Alternatively, finely divided powders of the two metals can be brought together and sintered to form what is essentially an alloy. Co-electrodeposition may also be used.

The alloy catalysts of the invention can be prepared in any convenient form of the types heretofore used for silver catalysts. Thus, the alloys can be formed as wire, gauze, machine turnings, pellets, etc. Additionally the alloy constituents can be supported upon various carriers, in conventional manner, it being sufficient for the purposes of the invention that the silver-gold alloy be exposed to the methanol to be reacted. The bulk or supported catalyst may be heated at an elevated temperature after fabrication to remove organic and other volatile impurities and form an optimum surface composition.

It will be understood by those skilled in the art of silver catalysis that, at the temperatures encountered in the formaldehyde process (550°-700° C.), the catalyst employed becomes sintered into a coherent porous mass having foramina extending throughout. During long periods of operation the foramina become plugged by carbon deposits resulting in an increase in pressure differential across the catalyst bed. Eventually the pressure differential is so large that the catalyst must be replaced. Difficulties are frequently encountered in removing the massed catalyst from equipment. One of the advantages of the silver-gold alloy catalyst is that during operation there is less sintering and surface rearrangement. Thus, although the alloy particles become compacted, they remain discrete. This allows the catalyst to operate for a longer period of time before high pressure differentials are encountered. Furthermore, the compacted catalyst is easily removed from equipment.

Use of a silver-gold alloy catalyst of this invention in formaldehyde production results in an improvement over the commercial silver catalysts in that for a given methanol conversion the yield of formaldehyde is higher. By "methanol conversion" is meant moles of methanol converted to other products per mole of methanol fed. By "yield of formaldehyde" is meant moles of formaldehyde formed per mole of methanol converted. The improved yield of formaldehyde is more evident at higher conversion rates. Thus at low conversion rates, about 50 mole %, an improvement of 1–2% in yield is realized while at high conversion rates, about 90 mole %, an improvement of 3–5% in yield is obtained. This improvement is graphically displayed in FIG. 1. Although the improvement may seem small, it has a tremendous impact on the production and energy costs of a commercial scale plant.

Although the mechanism by which the alloy improves the yield is not fully understood, data show that the use of the alloy decreases the $CO_2$ formed. The catalyst should contain from about 5 to 80 atomic % gold based upon the amount of gold-silver alloy. At higher amounts of gold an increase in CO formation is observed. At lower amounts of gold the reduction in $CO_2$ formation is not significant. It is preferred to use at least 20 atomic % gold to improve yield. For reasons of economy and yield, it is most preferred to use 40 to 60 atomic % gold.

The alloy catalyst may be readily substituted in commercial formaldehyde processes which use silver catalysts with little or no change in operating conditions.

As applied to the prior art processes, the silver-gold alloy catalyst improves the single stage yield of a low conversion system. However, the silver-gold alloy catalyst is particularly advantageous when used in a two-stage, generally high conversion system. Greatest improvement results when a silver-gold alloy catalyst is used in both stages of the system. If the silver-gold alloy catalyst is used in only one stage, then the standard silver catalyst is used in the other. In view of the high cost of silver-gold alloy catalyst, the preferred method of operation is with a standard silver catalyst in the first stage and the silver-gold alloy in the second stage. This configuration is preferred because the alloy catalyst in the second stage is exposed to a higher concentration of formaldehyde and the alloy catalyst is more selective in converting methanol without degenerating formaldehyde. Therefore, this configuration results in a higher formaldehyde yield.

The advantages of the invention can be seen by reference to the following examples:

The following general procedure was used to evaluate the catalysts of the invention. A 10 mm I.D. quartz tube was filled to a depth of 19.05 mm (¾") with the catalyst of choice which was usually in the form of irregular or polysurface granules in the 8-60 mesh (Tyler Equivalent) particle size range. The catalyst section was heated externally to initiate reaction and once initiated the external heat was adjusted to run the process at any desired temperature range. The bed and wall temperatures were recorded using appropriate thermocouples. When the catalyst was used in the first stage, liquid methanol (0.5 g/min) was vaporized, mixed with preheated air to furnish the desired oxygen to methanol ratio and passed through the catalyst bed at 550°–650° C. The product was analyzed by gas chromatography to determine yield and conversion. When the catalyst was used in the second stage, the procedure was similar except that the gaseous product stream obtained from Stage I was fed along with additional preheated air to the second stage.

Examination of the alloy catalyst at the conclusion of the experiments indicated that the granules were compacted and sintered but the material readily separated into discrete particles.

TABLE I

| No. | Catalyst Atomic % Ag | Catalyst Atomic % Au | Mole Ratio $O_2$/MeOH | Bed T °C. | Conv. MeOH % | Yield HCHO % |
|---|---|---|---|---|---|---|
| 1 | 100 | 0 | 0.208 | 550 | 51.2 | 94.3 |
| 2 | 50 | 50 | 0.210 | 550 | 52.6 | 95.7 |
| 3 | 100 | 0 | 0.261 | 580 | 68.4 | 92.9 |
| 4 | 40 | 60 | 0.280 | 565 | 68.0 | 93.6 |
| 5 | 100 | 0 | 0.333 | 610 | 82.4 | 90.7 |
| 6 | 40 | 60 | 0.337 | 600 | 83.1 | 92.3 |
| 7 | 100 | 0 | 0.358 | 655 | 87.4 | 87.9 |
| 8 | 40 | 60 | 0.368 | 635 | 89.8 | 91.1 |

Examples 1, 3, 5 and 7 are demonstrative of the systems known in the art which use a silver catalyst. Examples 2, 4, 6 and 8 are demonstrative of the claimed invention which employ a silver-gold alloy catalyst. A comparison of 1 and 2, 3 and 4, 5 and 6, and 7 and 8 indicates that for comparable methanol conversions the alloy catalyst results in a higher yield of formaldehyde.

As mentioned herein, FIG. 1 graphically shows the advantage of silver-gold alloy catalyst over the silver catalyst known in the art. The data for this figure was obtained from Examples No. 3 and 9–19. Examples 3 and 9–13 were obtained using a standard silver catalyst. Examples 14–19 were obtained using a 40 atomic % silver-60 atomic % gold catalyst. As is evident from FIG. 1, the alloy catalyst gives a greater yield of formaldehyde for a given conversion of methanol. Furthermore, compared to silver, the improvement in yield increases as the conversion increases.

TABLE II

| No. | Catalyst Atomic % Ag | Catalyst Atomic % Au | Mole Ratio $O_2$/MeOH | Bed T °C. | Conv. MeOH % | Yield HCHO % |
|---|---|---|---|---|---|---|
| 9 | 100 | 0 | 0.206 | 525 | 53.0 | 94.5 |
| 10 | 100 | 0 | 0.259 | 639 | 65.3 | 93.6 |
| 11 | 100 | 0 | 0.285 | 573 | 74.7 | 92.1 |
| 12 | 100 | 0 | 0.313 | 603 | 82.0 | 90.6 |
| 13 | 100 | 0 | 0.358 | 655 | 87.4 | 87.9 |
| 14 | 40 | 60 | 0.246 | 540 | 59.4 | 94.9 |
| 15 | 40 | 60 | 0.243 | 550 | 61.1 | 95.2 |
| 16 | 40 | 60 | 0.273 | 563 | 69.0 | 93.9 |
| 17 | 40 | 60 | 0.337 | 559 | 83.1 | 92.3 |
| 18 | 40 | 60 | 0.368 | 636 | 89.8 | 91.1 |
| 19 | 40 | 60 | 0.396 | 672 | 93.8 | 89.5 |

Table III illustrates the advantages of alloy catalyst when used in a two-stage system.

TABLE III

| No. | Stage I Catalyst Atomic % Ag | Stage I Catalyst Atomic % Au | Stage II Catalyst Atomic % Ag | Stage II Catalyst Atomic % Au | Bed Temperature Stage I | Bed Temperature Stage II | Mole Ratio $O_2$/MeOH Stage I | Mole Ratio $O_2$/MeOH Overall | Overall Conversion of MeOH % | Overall Yield of HCHO % |
|---|---|---|---|---|---|---|---|---|---|---|
| 20 | 100 | 0 | 100 | 0 | 535 | 660 | 0.208 | 0.490 | 97.6 | 84.6 |
| 21 | 40 | 60 | 50 | 50 | 595 | 580 | 0.297 | 0.463 | 97.5 | 89.0 |
| 22 | 40 | 60 | 50 | 50 | 510 | 500 | 0.216 | 0.483 | 98.0 | 89.6 |
| 23 | 100 | 0 | 40 | 60 | 565 | 520 | 0.268 | 0.444 | 98.3 | 87.4 |
| 24 | 100 | 0 | 40 | 60 | 525 | 560 | 0.206 | 0.448 | 98.6 | 88.1 |

Example 20 models a two-stage reactor system using silver catalyst. In comparison, Example 21 shows that the alloy catalyst for the same conversion rate obtains 4.4% higher yield.

The last three examples show the distinction between using the alloy catalyst in two stages (Example 22) versus using the alloy catalyst in the second stage and silver in the first stage (Examples 23 and 24). Although use of alloy catalyst in two stages results in the highest yield, the use of alloy catalyst in the second stage results in a significant improvement over silver catalysts (compare Examples 23 and 24 with 20). Thus, the advisability of using the alloy catalyst in one versus two stages is primarily an economic question which should be evaluated based on the size of the facility, and the cost of gold, methanol, formaldehyde, energy, etc.

Table IV displays the operability of several different alloy compositions.

TABLE IV

| No. | Catalyst Atomic % Ag | Catalyst Atomic % Au | Mole Ratio $O_2$/MeOH | Bed T °C. | Conv. MeOH % | Yield HCHO % |
|---|---|---|---|---|---|---|
| 25 | 25 | 75 | 0.209 | 530 | 47.1 | 95.4 |
| 26 | 25 | 75 | 0.233 | 550 | 57.6 | 95.6 |
| 27 | 50 | 50 | 0.210 | 550 | 52.6 | 95.7 |
| 28 | 50 | 50 | 0.282 | 600 | 72.1 | 94.1 |

Although there are no silver catalyst examples of corresponding methanol conversion, one may see by interpolation on FIG. 1 that the alloy compositions give an improved yield over the silver catalyst.

I claim:

1. In a process for selective oxidation/dehydrogenation of methanol to formaldehyde using a metal catalyst at a temperature of from 550 to 700° C. in a single or two-stage reaction system the improvement wherein the metal catalyst is a silver-gold alloy containing 5 to 80 atomic % gold in the single stage or in both stages of the two stage system.

2. The process of claim 1 in which a single stage reactor system is used.

3. The process of claim 1 in which the silver-gold alloy is 20 to 80 atomic % gold.

4. The process of claim 1 in which the silver-gold alloy is 40 to 60 atomic % gold.

5. The process of claim 1 in which the silver-gold alloy is supported upon a carrier.

6. The process of claim 1 wherein a two-stage reaction system is used.

7. The process of claim 6 wherein the silver-gold alloy is 20 to 80 atomic % gold.

8. The process of claim 6 wherein the silver-gold alloy is 40 to 60 atomic % gold.

9. The process of claim 6 wherein the silver-gold alloy is supported on a carrier.

10. The process of claim 2 wherein the silver-gold alloy is 20 to 80 atomic % gold.

11. The process of claim 2 wherein the silver-gold alloy is 40 to 60 atomic % gold.

12. The process of claim 2 wherein the silver-gold alloy is supported upon a carrier.

* * * * *